United States Patent [19]

Chin-Chan et al.

[11] Patent Number: 5,736,645
[45] Date of Patent: Apr. 7, 1998

[54] METHOD OF PREDICTING CRACK INITIATION BASED FATIGUE LIFE

[75] Inventors: Chu Chin-Chan, Ann Arbor; Angela Hubner, Dearborn, both of Mich.

[73] Assignee: Ford Global Technologies, Inc., Dearborn, Mich.

[21] Appl. No.: 783,723

[22] Filed: Jan. 16, 1997

[51] Int. Cl.$^6$ .............................. G01N 19/08; G01N 29/04
[52] U.S. Cl. .................................................. 73/799; 73/791
[58] Field of Search .......................... 73/760, 783, 787, 73/788, 789, 791, 799

[56] References Cited

U.S. PATENT DOCUMENTS

| | | | |
|---|---|---|---|
| 3,887,987 | 6/1975 | Salt | 73/789 |
| 4,590,804 | 5/1986 | Brull | 73/787 |
| 4,711,131 | 12/1987 | Hopkins | 73/799 |
| 4,875,170 | 10/1989 | Sakurai et al. | 73/799 |

OTHER PUBLICATIONS

"The Assessment and Use of Linear Static FFE Stress Analyses for Durability Calculations", by Peter Heyes, John Dakin and Christopher St. John, pp. 189–199. (No date).
"Analysis of Stain Gage Rosette Data for Fatigue Life Predictions" by J.W. Fash and F.A. Conle. (No date).

Primary Examiner—Richard Chilcot
Assistant Examiner—Max H. Noori
Attorney, Agent, or Firm—Frank G. McKenzie; Roger L. May

[57] ABSTRACT

A method of predicting crack initiation based fatigue life includes the steps of plotting the elastic finite element stress states of a stress history for a given component at a predetermined critical location in the stress space and determining the least square fit ellipsoid of the stress states by a straight line through the center of gravity. An aspect ratio $\lambda_2/\lambda_1$ is defined where $\lambda_1$ and $\lambda_2$ are the two largest eigen values of the eigen system of matrix M which defines the least square fit ellipsoid and where $\lambda_1 \geq \lambda_2$. A multiaxial fatigue analysis is performed where the aspect ratio exceeds a predetermined value.

14 Claims, 4 Drawing Sheets

METHOD OF PREDICTING CRACK INITIATION BASED FATIGUE LIFE

BACKGROUND OF THE INVENTION

1. Field of the Invention

The present invention relates generally to a method of predicting crack initiation based fatigue life of a component and, more specifically, to a method for quantifying the multiaxiality of a fatigue history such that additional fatigue analysis may be conducted and/or design parameters changed when the aspect ratio exceeds a predetermined value.

2. Description of the Related Art

Currently in the field of fatigue analysis and especially for fatigue analysis performed in the ground vehicle industry, predicting crack initiation based fatigue life of a component is most often based on the assumption that the stress history of the component in question is uniaxial. This assumption is made, among other reasons, to simplify the fatigue life calculations and in most cases is reasonable under the circumstances. The uniaxial approach has been extended to each element in a component as well as full vehicle finite element models which are subject to loading that induce proportional stress states. Under proportional loading, the variation of the major principal stress is analyzed in the same way as it is in the uniaxial case.

However, despite the common assumption of uniaxial stress history to facilitate fatigue life calculations, where the degree of multiaxiality of the component does not justify the assumption, a uniaxial fatigue analysis can overpredict fatigue life by more than a factor of ten.

The multiaxial fatigue analysis differs from the uniaxial approach in that a multiaxial damage parameter is used and the critical plane approach is employed in the analysis. More specifically, the multiaxial damage parameter takes into account the contribution to fatigue damage from both the tensile and shear components of the stress and strain variations. The uniaxial approach involves only the tensile component.

Using the critical plane approach involves a fatigue analysis on all planes before the most damaged plane can be determined. Obviously, an infinite number of planes could be considered when "all planes" are analyzed and so such an effort is not practical. However, even where a descretized critical plane approach is employed, the computational time for implementing the multiaxial fatigue method is prohibitive. For example, for the simpler surface elements in which plane stress conditions prevail, a search every ten degrees for the critical plane will increase the computational time performing multiaxial fatigue analysis by a factor of eighteen over that using uniaxial approaches. For general solid elements with three dimensional stresses, the computational time factor will become 162.

Currently, in the related art, a principal stress versus principal direction angle plot is used together with a major principal stress versus minor principal stress plot to help visualize whether the proportional loading assumption is acceptable. A graphical stress plot has also been suggested to serve the same purpose. Neither of these approaches provide a quantitative measurement to enable automatic multiaxiality detection. Rather, they are dependent on the experience of the observer and for that reason, current methods are entirely subjective. Thus, there is a need in the art for a method for quantifying the multiaxiality of stress histories such that a determination may be made between a simple uniaxial fatigue analysis and a more accurate multiaxial fatigue analysis for fatigue life prediction.

SUMMARY OF THE INVENTION

The present invention is a method of predicting crack initiation based fatigue life and includes the steps of plotting the elastic finite element stress states of a stress history for a given component at a predetermined critical location in a stress space. The least square fit ellipsoid of the stress state is determined by a straight line through its center of gravity. An aspect ratio $\lambda_2/\lambda_1$ is then defined where $\lambda_2$ and $\lambda_1$ are the two largest eigen values of the eigen system of a matrix M which defines the least square fit ellipsoid and where $\lambda_1 \geq \lambda_2$. A multiaxial fatigue analysis is then performed only where the aspect ratio $\lambda_2/\lambda_1$ exceeds a predetermined value.

One advantage of the method of the present invention is that it is computationally efficient. It does not require principal stress direction calculations for individual stress states in a history. Another advantage of the method of the present invention is that the major principal stress direction is easily determined and the multiaxiality of a history is measured about the coordinate independent major principal stress direction. The multiaxiality measure can also be calibrated to make the uniaxial/multiaxial switch automatically. Still another advantage of the method of the present invention is that the method can be extended to three dimensional cases where the identification of principal stress direction and the most critical fatigue failure plane is likely to save major computational efforts.

Other features and advantages of the present invention will be readily appreciated as the same becomes better understood after reading the subsequent description when considered in connection with the accompanying drawings.

DESCRIPTION OF THE PREFERRED EMBODIMENT(S)

The present invention is directed toward a method of predicting crack initiation based fatigue life of a component. In practicing the method, a component, such as a vehicle body, a shaft, shock tower, pressure vessel and the like, which is often the subject of fatigue life analysis, is cyclically loaded to generate a stress (σ) history. More specifically, load cells may be mounted to the component in question for the purpose of recording the stresses generated on the component during the loading period. Depending on the component in question, it may then be mounted to a test fixture in a lab and subjected to cyclic loading. Alternatively, the component, such as a vehicle body, may be loaded by operating the vehicle on a proving ground over predetermined road conditions such that the vehicle body is subjected to certain types of loads. The results of these loadings are recorded via the load cells by computer. A finite element analysis is then conducted to obtain the stress history.

Figure 1:
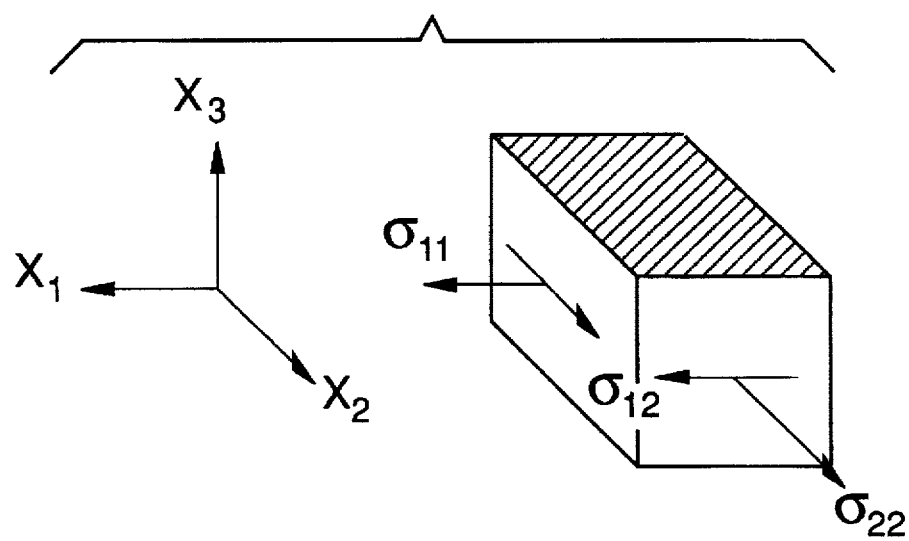
FIG. 1 is a schematic diagram of plane stresses acting on a surface finite element.

The method of the present invention includes the step of plotting the elastic finite element stress states of a stress history for a given component at a predetermined location in a stress space. FIG. 1 illustrates the plane stresses acting a surface finite element of a structural model. As shown here, the surface normal coincides with the $x_3$ axis. Although the method of the present invention can be employed to analyze general three dimensional stress histories, to better illustrate the method, only two dimensional plane stress histories that are experienced by surface elements where fatigue cracks usually starts are discussed in detail here.

The stress history can be defined as proportional if the stress ratios:

$$\frac{\sigma_{12}}{\sigma_{11}} \text{ and } \frac{\sigma_{22}}{\sigma_{21}}$$

remain constant throughout the loading history. That is, stress states during a proportional loading history fall on a straight line that passes through the origin of the $\sigma_{11}$-$\sigma_{22}$-$\sigma_{12}$ space. However, a realistic stress history rarely fits such a straight line description due to either data scattering or the multiaxial nature of the loading history. The method of predicting fatigue crack initiation in a component of the present invention is employed to quantify the deviation of a real stress history from a proportional one. The method includes determining the least square fit line through the center of gravity of the stress state. This is accomplished as follows:

The mean stress state is denoted by $$[(\sigma_{11})_o (\sigma_{22})_o (\sigma_{12})_o]$$

which is determined by $$\left[ \frac{1}{N} \sum_i (\sigma_{11})_i, \frac{1}{N} \sum_i (\sigma_{22})_i, \frac{1}{N} \sum_i (\sigma_{12})_i \right]$$

where $1 \leq I \leq N$, and N is the total number of data points in the stress space. A simplified notation can then be introduced for the $i_{th}$ stress state with respect to the mean stress state: $[x_i\ y_i\ z_i]$, which is defined by $$[(\sigma_{11})_i - (\sigma_{11})_o, (\sigma_{22})_i - (\sigma_{22})_o, (\sigma_{12})_i - (\sigma_{12})_o]$$

Assuming that the least square fit line is in the direction defined by a unit vector $[\alpha\ \beta\ \gamma]$, then this direction can be determined by minimizing the distance function $$\sum_{i=1}^{N} d_i^2 = \sum_{i=1}^{N} [x_i^2 + y_i^2 + z_i^2 - (\alpha x_i + \beta y_i + \gamma z_i)^2].$$

Using the standard Lagrangian formulation to minimize the above function while satisfying the constraint that the aforementioned $[\alpha\ \beta\ \gamma]$ is a unit vector, leads to the Lagrange function:

$$\sum_{i=1}^{N} [x_i^2 + y_i^2 + z_i^2 - (\alpha x_i + \beta y_i + \gamma z_i)^2] + \lambda(\alpha^2 + \beta^2 + \gamma^2 - 1),$$

where $\lambda$ is the Lagrange multiplier. The direction $[\alpha\ \beta\ \gamma]$ is determined by setting the partial derivative of the Lagrange function with respect to $\alpha$, $\beta$ and $\gamma$ to zero:

$$\alpha(\Sigma x_i^2 - \lambda) + \beta \Sigma x_i y_i + \gamma \Sigma x_i y_i = 0$$

$$\alpha \Sigma y_i x_i + \beta(\Sigma y_i^2 - \lambda) + \gamma \Sigma y_i z_i = 0$$

$$\alpha \Sigma z_i x_i + \beta \Sigma z_i y_i + \gamma(\Sigma z_i^2 - \lambda) = 0$$

Solving the above equations is equivalent to solving for the eigen system of matrix M, defined by:

$$M = \begin{pmatrix} \Sigma x_i^2 & \Sigma x_i y_i & \Sigma x_i z_i \\ \Sigma x_i y_i & \Sigma y_i^2 & \Sigma y_i z_i \\ \Sigma x_i z_i & \Sigma y_i z_i & \Sigma z_i^2 \end{pmatrix}$$

The matrix M is related to the moment of inertia matrix J for a distribution by:

$$J = \Sigma(x_i^2 + y_i^2 + z_i^2)I - M$$

Where I denotes a 3×3 identity matrix. As illustrated in the equation above, the eigen vectors of matrix M are identical to those of J. Thus, the major axes determined by the current least square fit coincide with the principal axes of the moment of inertia ellipsoid. Further, the three eigen values of matrix M differ from the three principal moments of inertia, respectively, by a constant value expressed as $\Sigma(x_i^2 + y_i^2 + z_i^2)$.

The eigen system of matrix M defines a least square fit ellipsoid of which the axes are the orthogonal eigen vectors and the length of the axes are the eigen values of M. The eigen values are arranged in algebraic order and denoted as $\lambda_1 (\geq) \lambda_2, (\geq) \lambda_3$. The larger of the two ratios here, $\lambda_2/\lambda_1$ is referred to as an aspect ratio. The aspect ratio is employed as a measure of multiaxiality of the stress history of the component in question. More specifically, where the aspect ratio $\lambda_2/\lambda_1$ exceeds a predetermined value as discussed in greater detail below, a multiaxial fatigue analysis, rather than a uniaxial fatigue analysis may be employed.

Although the distribution of the stress history and hence the least square fit line may appear different in the $\sigma_{11}$-$\sigma_{22}$-$\sigma_{12}$ space, and do depend on the $x_1$-$x_2$-$x_3$ coordinate system in which the stress history is expressed, the stress proportionality of the majority of the fatigue events is independent of the $x_1$-$x_2$-$x_3$ coordinate system. That is, the principal stress axes for the majority of the fatigue events is coordinate system independent. In the plane stress cases discussed here, the principal stress axes denoted $x'_1$- and $x_2'$-axes, can be defined by their counterclockwise rotational angle about the $x_3$ axis relative to the given $x_1$- and $x_2$ axes as follows:

$$\theta = 1/2 \tan^{-1} \frac{2\gamma_1}{\alpha - \beta}$$

A coordinate independent aspect ratio therefore can be obtained by performing the least square fit on stress states $[\sigma_{1'1'}, \sigma_{2'2'}, \sigma_{1'2'}]$ expressed in the newly determined principal $x'_1$-$x'_2$ coordinate system. By using this technique, a coordinate independent aspect ratio may be obtained.

Figure 2:
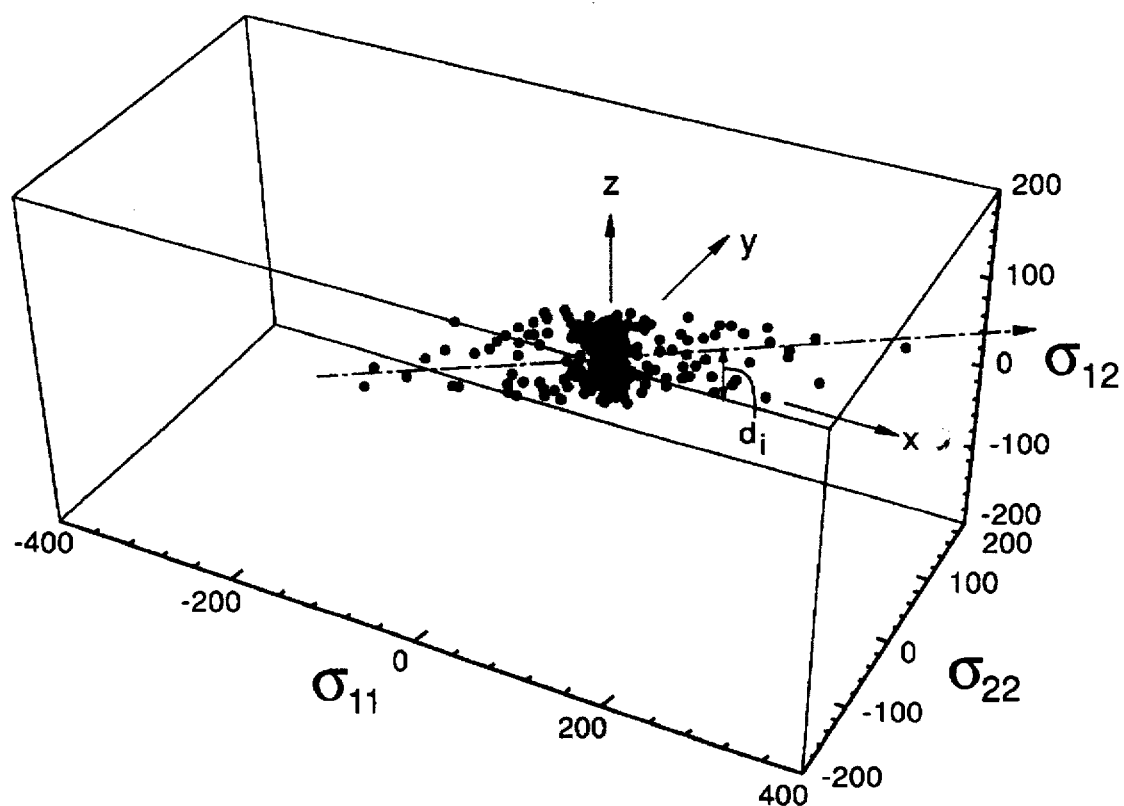
FIG. 2 is a distribution of a plane stress history in a stress space experienced by a surface element which is least square fitted.

When the aspect ratio is small and the least square fit line goes through the close neighborhood of the origin of the stress space as illustrated in FIG. 2, a uniaxial analysis is adequate to predict fatigue life. However, to determine a quantitative threshold aspect ratio for switching between uniaxial and multiaxial analysis requires a detailed case study to correlate the multiaxiality measure with the difference in fatigue life predicted by uniaxial and multiaxial analysis. An example follows.

The distributions in a stress space of a number of histories with various degrees of multiaxiality are analyzed using multiaxial fatigue methods such as those described by C. C. Chu, F. A. Conle and J. J. Bonnen in the article entitled "Multiaxial Stress-Strain Modeling and Fatigue Life Prediction of SAE Axle Shafts" ASTM STP 1191, pages 37–54, (1993) and which is incorporated herein by reference. The materials in question are assumed to be SAE 1045 steels. Two biaxial damage criteria, the modified Smith-Watson-Topper ($C_{swt}$) and Brown and Miller's with Socie's mean stress correction (BMS) are used in such an analysis. Both the calculated aspect ratio and the predicted fatigue life error are reported below in Table 1. The predicted fatigue life is expressed by the factor $(N_f)_{uni}/(N_f)_{multi}$, which indicates the error associated with using uniaxial methods to predict fatigue life when the loading is multiaxial. The uniaxial life prediction $(N_f)_{uni}$ here is obtained by analyzing the stress history in the major principal stress direction and assuming that all the other stress components are zero.

|  | (a) | (b) | (c) | (d) | (e) | (f) |
|---|---|---|---|---|---|---|
| Aspect Ratio $\lambda_2/\lambda_1$ | 0.01 | 0.07 | 0.16 | 0.28 | 0.44 | 0.58 |
| $(N_f)_{uni}/(N_f)c_{swt}$ | 1.08 | 1.22 | 1.56 | 1.67 | 2.63 | 4.17 |
| $(N_f)_{uni}/(N_f)_{BMS}$ | 1.00 | 1.15 | 1.49 | 2.04 | 3.03 | 5.00 |

Table 1 Predicted fatigue life and aspect ratio for stress histories discussed above. $(N_f)_{uns}$ for criterion $C_{swt}$ is $10^{5.71}$, $(N_f)_{uns}$ for criterion BMS is $10^{5.98}$.

Figure 3:
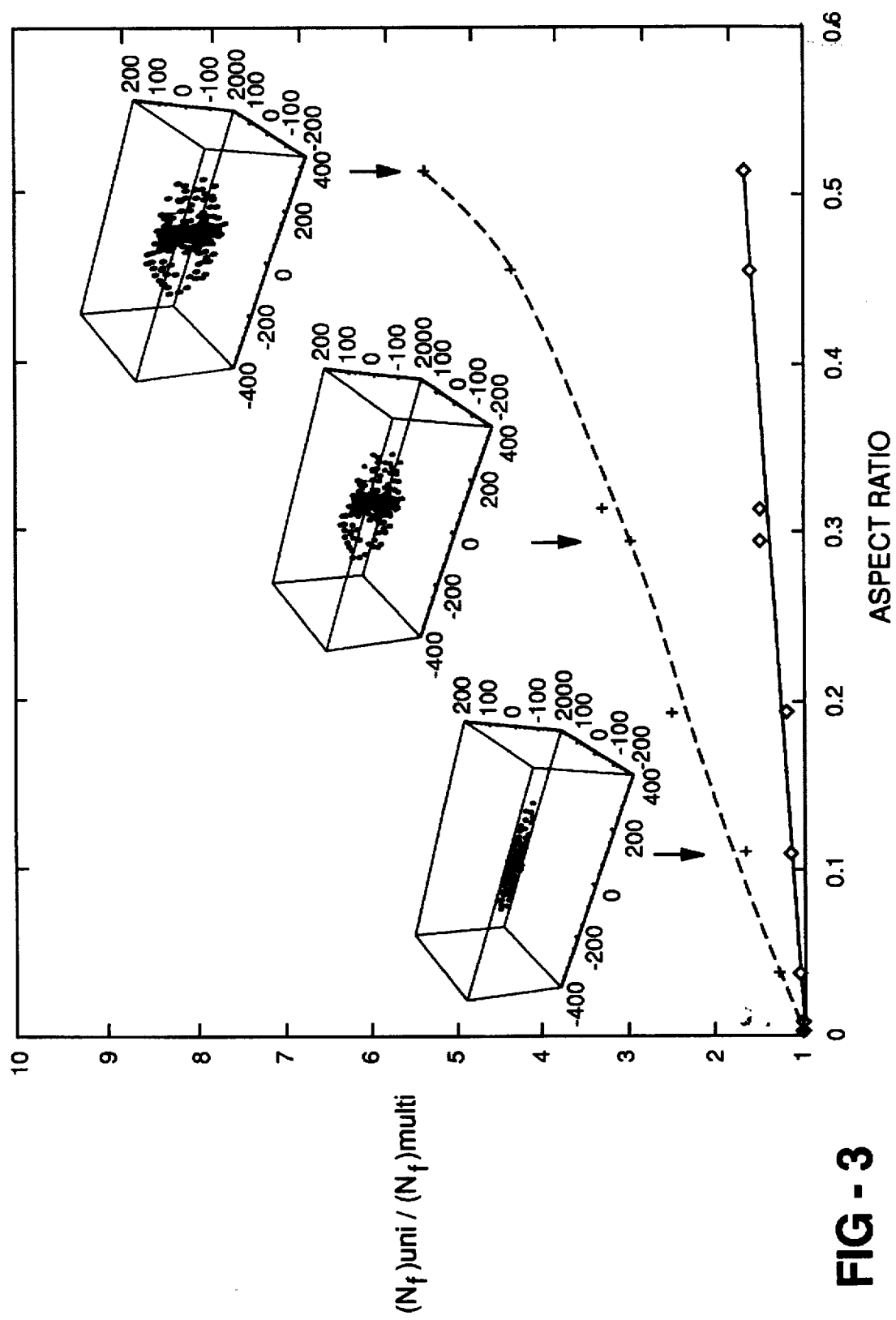
FIG. 3 is a graph of fatigue life error versus aspect ratio.
Figure 4:
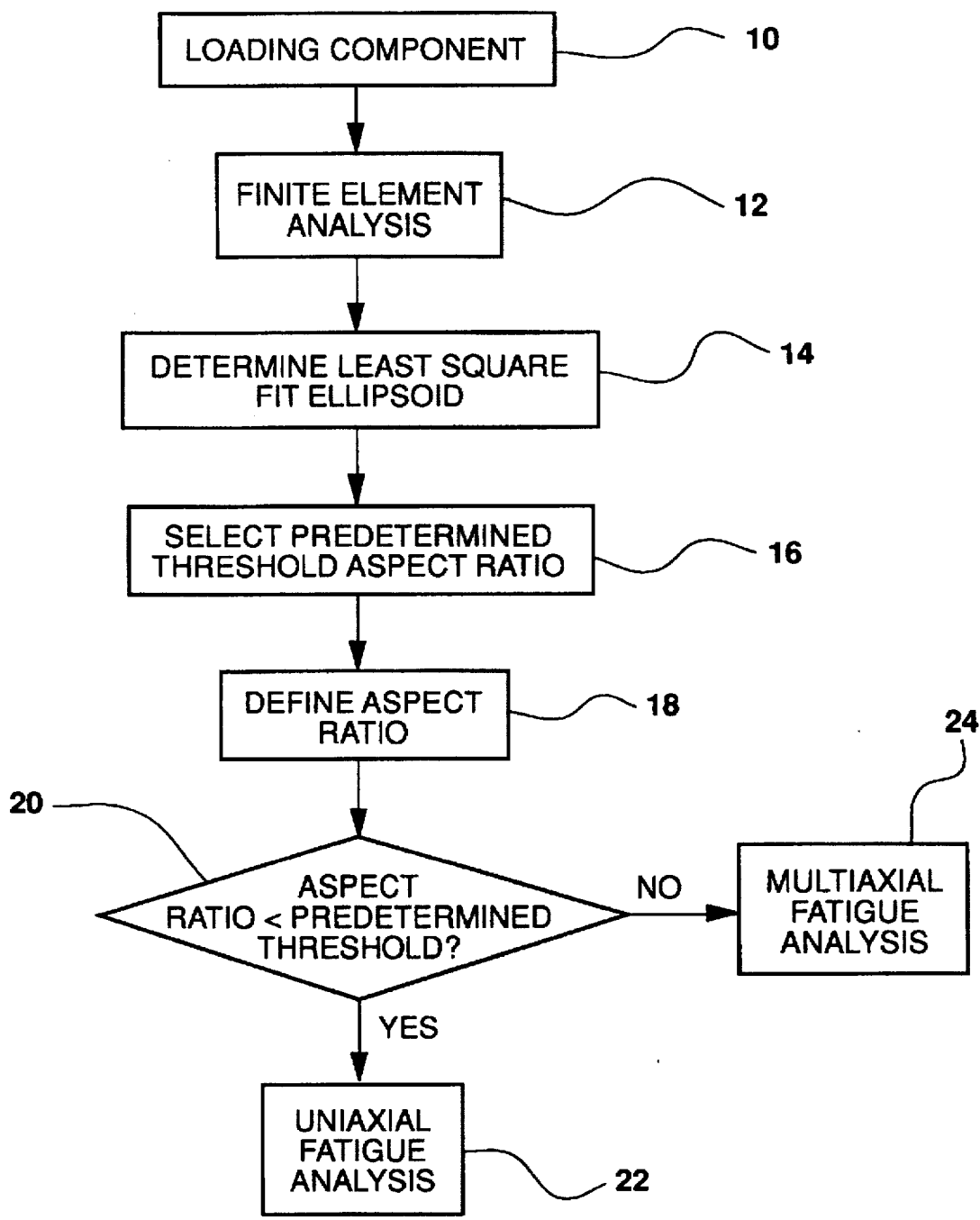
FIG. 4 is a flowchart illustrating the method of the present invention.

The establishment of quantitative guidelines for the number of analyzed planes requires correlation between the calculated aspect ratio and the uniaxial methods error in identifying the most critical plane. The fatigue life prediction error expressed by the factor $(M_f)_{uni}/(M_f)_{multi}$ is plotted in FIG. 3 against the aspect ratio. As illustrated in the flowchart of FIG. 4, a method, according to the present invention, is used for predicting crack initiation of a component based on fatigue life. In block 10, a component is loaded and a finite element analysis of the stress history is conducted at block 12. The least square fit ellipsoid is then determined at 14. An aspect ratio threshold value is chosen at 16 such that when the aspect ratio 18 is less than the predetermined value as shown at 20, fatigue analysis is needed only on the plane identified by the least square fit line as indicated at block 22. When the aspect ratio is larger than the predetermined value, a full scale multiaxial analysis or, a search over the complete 180 degree range of plane angles, is necessary to find the most critical plane as indicated at 24.

Figure 5:
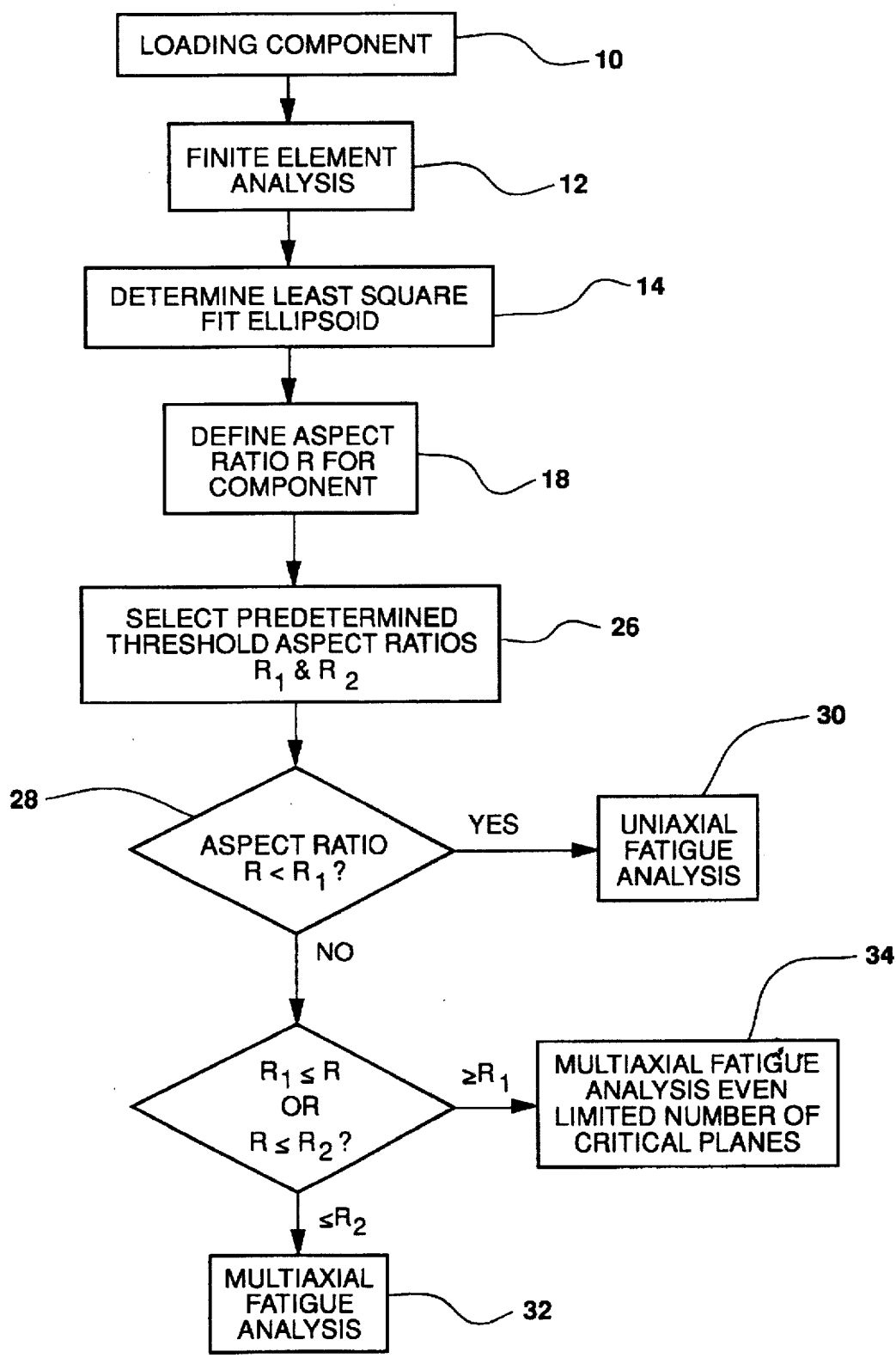
FIG. 5 is a flowchart illustrating an alternate method of the present invention.

Another embodiment of the method according to the present invention is illustrated in the flowchart of FIG. 5. In block 26 two aspect ratio threshold values $r_1$ and $r_2$ may be chosen such that when the aspect ratio is less than $r_1$ as indicated at 28, fatigue analysis is needed only on the plane identified by the least square fit line as shown by block 30. When the aspect ratio is larger than $r_2$, a full scale multiaxial analysis 32 is necessary to find the most critical plane. For aspect ratios between $r_1$ and $r_2$, the number of planes analyzed is increased proportionally as indicated at 34. It has been found that values 0.01 and 0.3 seem appropriate selections for $r_1$ and $r_2$, respectively.

Where the aspect ratio justifies a multiaxial fatigue analysis, and the predicted fatigue life error is significant, the design parameters of the component may be adjusted to increase the fatigue life thereof. For example, and depending on the component in question, any given cross section may be thickened or the geometry of the component may be changed such that a uniaxial fatigue principals may be applied. Alternatively, additional or different materials may be employed for the component which are better suited for withstanding the multiaxial stresses to which the component is subjected.

Use of the present method of predicting crack initiation based fatigue life eliminates the need for multiaxial analysis where the aspect ratio falls below the predetermined amount. Furthermore, the use of the method of the present invention is coordinate independent and the multiaxiality measure can be calibrated to make the uniaxial/multiaxial switch automatically. The method of the present invention can also be extended to three dimensional cases where the ability to identify the principal stress direction will save major computational efforts.

The present invention has been described in an illustrative manner. It is to be understood that the terminology which has been used is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A method of predicting crack initiation based fatigue life, said method including the steps of:

plotting elastic finite element stress states of a stress history for a given component at a predetermined location in a stress space;

determining a least square fit ellipsoid of the stress states by a straight line through a center of gravity;

defining an aspect ratio $\lambda_2/\lambda_1$, where $\lambda_1$ and $\lambda_2$ are the two largest eigen values of an eigen system of matrix M which defines the least square fit ellipsoid and where $\lambda_1 \geq \lambda_2$; and performing a multiaxial fatigue analysis where the aspect ratio $\lambda_2/\lambda_1$ exceeds a predetermined value.

2. A method as set forth in claim 1 further including the step of performing limited multiaxial fatigue analysis over a predetermined number of critical planes where the aspect ratio is between two predetermined values.

3. A method as set forth in claim 1 further including the steps of performing a uniaxial fatigue analysis where the aspect ratio is less than a predetermined value.

4. A method as set forth in claim 1 further including the step of adjusting design parameters of the component so as to increase the fatigue life of the component.

5. A method as set forth in claim 1 further including the steps of determining the fatigue life error and comparing the fatigue life error versus the aspect ratio to determine a threshold, predetermined value of said aspect ratio.

6. A method as set forth in claim 1 further including the steps of subjecting the component to loading conditions such that a stress history may be generated.

7. A method as set forth in claim 6 further including the step of recording the stress history generated through load cells mounted to the component.

8. A method of predicting crack initiation based fatigue life, said method including the steps of:

plotting elastic finite element stress states of a stress history for a given component at a predetermined location in a stress space;

determining a least square fit ellipsoid of the stress states by a straight line through a center of gravity;

defining an aspect ratio $\lambda_2/\lambda_1$, where $\lambda_1$ and $\lambda_2$ are the two largest eigen values of an eigen system of matrix M which defines the least square fit ellipsoid and where $\lambda_1 \geq \lambda_2$; and performing a uniaxial fatigue analysis where the aspect ratio is less than a predetermined value.

9. A method as set forth in claim 8 further including the step of performing a multiaxial fatigue analysis where the aspect ratio exceeds a predetermined value.

10. A method as set forth in claim 8 further including the step of performing limited multiaxial fatigue analysis over a predetermined number of critical planes where the aspect ratio is between two predetermined values.

11. A method as set forth in claim 8 further including the step of adjusting design parameters of the component so as to increase the fatigue life of the component.

12. A method as set forth in claim 8 further including the steps of determining the fatigue life error and comparing the fatigue life error versus the aspect ratio to determine a threshold, predetermined value of said aspect ratio.

13. A method as set forth in claim 8 further including the steps of subjecting the component to loading conditions such that a stress history may be generated.

14. A method as set forth in claim 13 further including the step of recording the stress history generated through load cells mounted to the component.

* * * * *